United States Patent
Jensen et al.

(10) Patent No.: US 7,680,540 B2
(45) Date of Patent: Mar. 16, 2010

(54) MULTI-APPLICATION TRIAL STIMULATOR

(75) Inventors: Steven L. Jensen, Andover, MN (US); Allen D. Almendinger, Bloomington, MN (US); Christopher M. Arnett, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 1159 days.

(21) Appl. No.: 11/194,088

(22) Filed: Jul. 29, 2005

(65) Prior Publication Data

US 2007/0027501 A1 Feb. 1, 2007

(51) Int. Cl.
*A61N 1/08* (2006.01)
(52) U.S. Cl. ........................................ 607/60
(58) Field of Classification Search .............. 607/2, 607/48, 63; 600/547
See application file for complete search history.

(56) References Cited

U.S. PATENT DOCUMENTS

| | | | |
|---|---|---|---|
| 5,571,148 A | | 11/1996 | Loeb et al. |
| 6,360,750 B1 | | 3/2002 | Gerber et al. |
| 6,687,538 B1 | * | 2/2004 | Hrdlicka et al. ............. 607/2 |
| 6,754,533 B1 | | 6/2004 | Helfinstine et al. |
| 2001/0041920 A1 | | 11/2001 | Starkweather et al. |
| 2002/0055761 A1 | | 5/2002 | Mann et al. |
| 2002/0077561 A1 | | 6/2002 | Jamar et al. |
| 2002/0147485 A1 | | 10/2002 | Mamo et al. |
| 2003/0120323 A1 | * | 6/2003 | Meadows et al. ............. 607/46 |
| 2003/0171789 A1 | * | 9/2003 | Malek et al. ................ 607/60 |
| 2004/0111130 A1 | | 6/2004 | Hrdlicka et al. |

(Continued)

FOREIGN PATENT DOCUMENTS

WO    WO 98/29160    7/1998

(Continued)

OTHER PUBLICATIONS

Notification of Transmittal of the International Search Report and the Written Opinion of the International Search Authority, dated Nov. 20, 2006 for corresponding PCT Application No. PCT/US2006/029071, filed Jul. 26, 2006 (13 pgs.).

(Continued)

*Primary Examiner*—Carl H. Layno
*Assistant Examiner*—Jon-Eric C. Morales
(74) *Attorney, Agent, or Firm*—John W. Albrecht; Stephen W. Bauer; Shumaker & Sieffert, P.A.

(57) ABSTRACT

The disclosure relates to an electrical trial stimulator that stores multiple applications to selectively emulate the operation of different chronically implanted stimulators. Each application corresponds to a different chronically implanted stimulator. Upon selection of a particular application, the stimulator executes a set of instructions to emulate the operation of a chronically implanted stimulator that corresponds to the application. The multi-application stimulator permits a physician to select an application for stimulation therapy, and evaluate efficacy of a particular chronically implanted stimulator. In addition, the physician may select any of the other stimulation applications to emulate other stimulators. The different stimulation applications may correspond to different stimulators that deliver a similar therapy, e.g., stimulators designed to deliver spinal cord stimulation for alleviation of chronic pain. Alternatively, the applications may correspond to stimulators that deliver different types of therapy, e.g., stimulators that deliver spinal cord, deep brain, gastrointestinal, or pelvic floor stimulation.

47 Claims, 3 Drawing Sheets

U.S. PATENT DOCUMENTS

| | | | |
|---|---|---|---|
| 2004/0215287 A1 | 10/2004 | Swoyer et al. | |
| 2005/0066088 A1 | 3/2005 | Helfinstine et al. | |
| 2005/0075669 A1 | 4/2005 | King | |
| 2005/0107841 A1 | 5/2005 | Meadows et al. | |
| 2005/0131493 A1 | 6/2005 | Boveja et al. | |
| 2005/0182458 A1 | 8/2005 | Goedeke | |
| 2007/0021804 A1* | 1/2007 | Maltan et al. | 607/55 |

FOREIGN PATENT DOCUMENTS

| | | |
|---|---|---|
| WO | WO 03/061761 | 7/2003 |

OTHER PUBLICATIONS

Notification of Transmittal of the International Preliminary Report on Patentability for corresponding PCT Application No. PCT/US2006/029071, filed Jul. 26, 2006 (8 pgs.).

Reply to Written Opinion for corresponding PCT Application No. PCT/US2006/029071, dated May 17, 2007 (5 pgs.).

"Spinal Cord Stimulation, Patient Management Guidelines for Clinicians", Chapter 4, Devices and Their Operation, Medtronic, Inc. pp. 17-25, (1999).

* cited by examiner

MULTI-APPLICATION TRIAL STIMULATOR

TECHNICAL FIELD

The invention relates to medical devices and, more particularly, external electrical stimulators.

BACKGROUND

Electrical stimulation is an effective therapy for a variety of conditions and diseases that adversely affect patient health. For example, electrical stimulation has been effective in alleviating chronic pain, movement disorders, gastrointestinal disorders, and pelvic floor disorders. Spinal cord stimulation systems have been found to provide relief for chronic pain. Deep brain stimulation can be effective in treatment of movement disorders such as Parkinson's disease, as well as other neurological disorders such as epilepsy. Stimulation of the gastrointestinal tract can be effective in alleviating gastroparesis and obesity. Stimulation of the pelvic floor can be effective in alleviating urinary incontinence, fecal incontinence, pelvic pain, and sexual dysfunction.

Typically, electrical stimulation is delivered by an implantable pulse generator that is chronically implanted within the patient. One or more leads extending from the implantable pulse generator carry electrodes for delivery of stimulation energy to a target tissue or nerve site. Unfortunately, some patients may not respond to stimulation therapy. For this reason, a physician often prescribes a course of trial or "screening" stimulation to evaluate the likely efficacy of electrical stimulation therapy for the patient. In particular, an external trial stimulator is used to evaluate the efficacy of stimulation before implanting a chronic stimulator. A chronic stimulator typically requires surgical implantation and may be implanted for several years.

An external trial stimulator is ordinarily electrically coupled to one or more implanted leads through a percutaneous extension. The trial stimulator may be carried by the patient, e.g., at the waist. The physician penetrates through the skin and tunnels the leads to a target site. Upon connection of the leads to the external trial stimulator, trial stimulation is activated to emulate the therapy delivered by a chronically implanted stimulator. Although the trial stimulator may only be used for a short time, e.g., a period of hours, days or weeks, the patient and physician are able to determine if the stimulation therapy is effective in alleviating the symptoms.

If the therapy is successful, the patient may undergo surgery to implant a chronic stimulator. If the trial therapy is unsuccessful, the physician may alter the trial stimulation, try another type of stimulation therapy, or abandon stimulation therapy. In the case of an unsuccessful therapy, the use of the external trial stimulator is beneficial in avoiding the need to implant and then explant a chronically implanted device. In this way, the time, labor, patient risk, and patient discomfort associated with surgical implantation and explantation can be avoided. On the other hand, successful trial therapy provides heightened confidence in the efficacy of chronic implantation, and may reveal desirable stimulation parameter settings to be programmed into the implantable stimulator.

SUMMARY

The disclosure is directed to a trial electrical stimulator that stores a set of instructions associated with multiple applications to selectively emulate the operation of different chronically implanted stimulators. The trial stimulator may be a neurostimulator that operates in conjunction with electrodes carried by one or more implanted leads. Each application corresponds to a different chronically implanted stimulator and may be associated with a set of instructions. Upon selection of a particular application, the trial stimulator emulates the operation of a chronically implanted stimulator that corresponds to the application.

The trial stimulator may reside externally to the patient and connect to one or more implanted leads via a percutaneous extension. The multi-application trial stimulator permits a physician to select an application for stimulation therapy, and thereby evaluate the efficacy of a particular type of chronically implanted stimulator. In addition, the physician may readily select any of the other stimulation applications to emulate other implanted stimulators. In this manner, the physician may switch between different stimulation applications, as desired. A patient programmer or physician programmer may be used to control the multi-application trial stimulator.

The different stimulation applications may correspond to different stimulators that deliver a similar therapy. For example, the applications may correspond to two or more stimulators designed to deliver spinal cord stimulation for alleviation of chronic pain. Alternatively, the applications may correspond to stimulators that deliver different types of therapy. For example, the applications may correspond to stimulators that deliver spinal cord stimulation, deep brain stimulation, gastrointestinal stimulation, or pelvic floor stimulation. In some embodiments, the applications may correspond to different types of therapy, as well as different stimulators designed to deliver each type of therapy. In addition, the applications may be targeted to particular types of disorders.

In one embodiment, the invention provides an electrical stimulation system comprising a trial stimulator and a programmer. The trial stimulator generates electrical stimulation pulses, the trial stimulator having a memory storing multiple sets of instructions, wherein each set of instructions corresponds to one of a plurality of different chronic stimulators. The programmer programs the trial stimulator to select one of the sets of instructions for operation of the trial stimulator. The trial stimulator applies the selected set of instructions to emulate operation of a corresponding chronic stimulator.

In another embodiment, the invention provides an electrical stimulator comprising a stimulation pulse generator that generates electrical stimulation pulses, a memory storing multiple sets of instructions, wherein each set of instructions corresponds to one of a plurality of different chronic stimulators, and a processor that selects one of the sets of instructions to control operation of the stimulation pulse generator, wherein the processor applies the selected set of instructions to emulate operation of a corresponding chronic stimulator.

In an additional embodiment, the invention provides a method comprising storing multiple sets of instructions in a memory in a trial electrical stimulator, wherein each set of instructions corresponds to one of a plurality of different chronic stimulators, and selecting one of the sets of instructions to control operation of a stimulation pulse generator within the trial electrical stimulator, wherein the processor applies the selected set of instructions to emulate operation of a corresponding chronic stimulator.

In various embodiments, the invention may provide one or more advantages. For example, storing a plurality of stimulation applications within one trial stimulator may enable the use of a single trial stimulator to evaluate a variety of stimulation therapies. In comparison to the use of different trial stimulators for different stimulation applications, the use of a single, more versatile trial stimulator can simplify evaluation by the physician and reduce the cost of trial stimulation. In particular, there is no need to use multiple trial stimulators dedicated to emulation of individual chronic stimulators. In addition, the use of a single patient programmer to control delivery of therapy by a trial stimulator eliminates the need for the patent to learn how to operate different types of patient programmers. The use of a single universal patient programmer also may reduce patient confusion.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
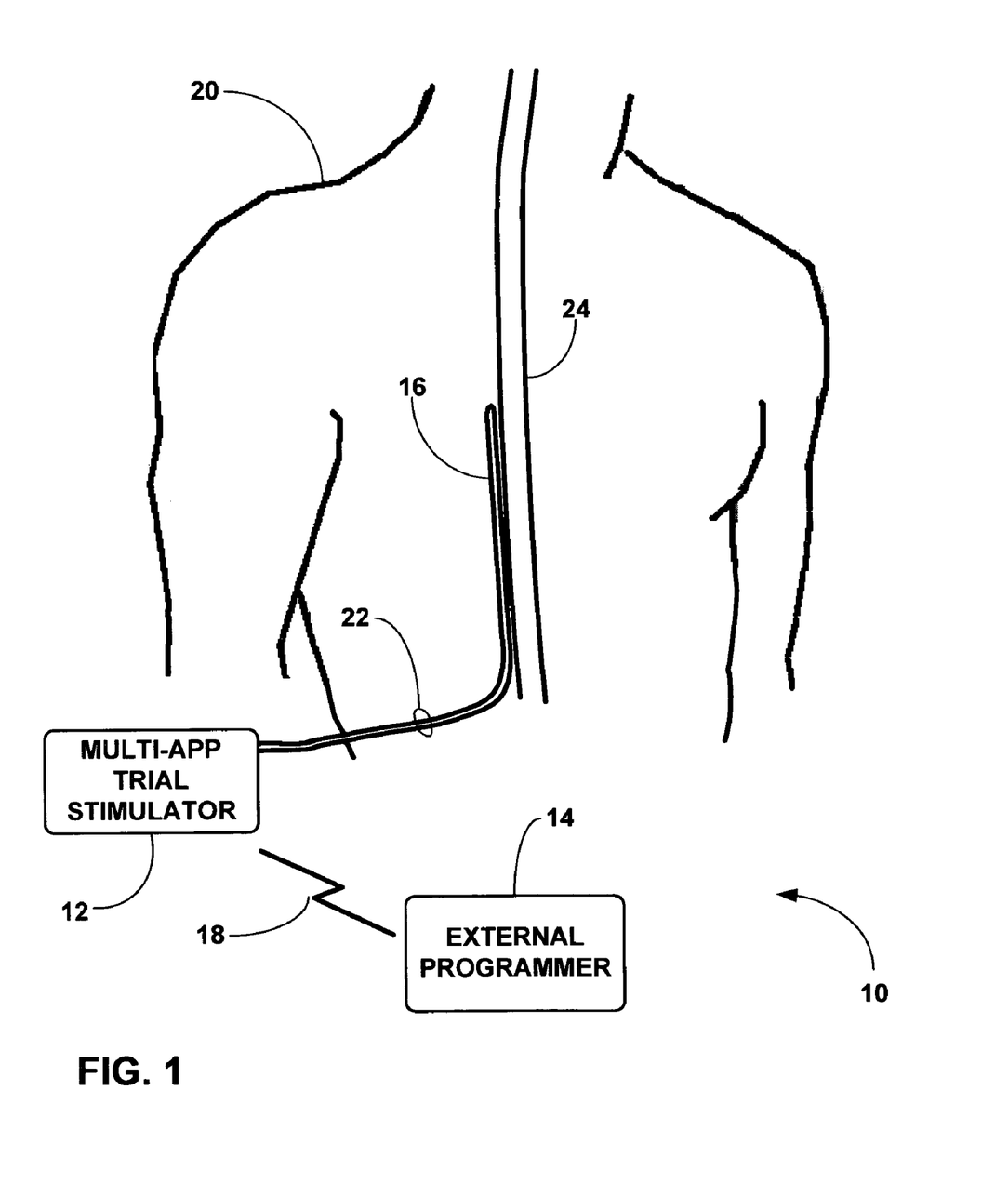
FIG. 1 is a diagram illustrating a trial stimulation system incorporating a multi-application trial stimulator for evaluating the efficacy of electrical stimulation.

FIG. 1 is a diagram illustrating a trial stimulation system 10 for evaluating the efficacy of electrical stimulation. In FIG. 1, for purposes of illustration, system 10 is configured for spinal cord stimulation. However, system 10 may be adapted for a variety of therapies, including spinal cord stimulation, deep brain stimulation, gastrointestinal tract stimulation, pelvic floor stimulation, and muscle stimulation. In addition, system 10 may deliver therapies designed to alleviate a variety of disorders, such as chronic pain, movement disorders, gastrointestinal disorders, and pelvic floor disorders. Accordingly, the application of system 10 to spinal cord stimulation in the example of FIG. 1 is for purposes of illustration and should not be considered limiting of the invention as broadly embodied and described.

As shown in FIG. 1, system 10 includes a trial stimulator 12, an external programmer 14, and an implantable lead 16. External programmer 14 communicates with trial stimulator 12 by wired communication or wireless communication, as indicated by reference numeral 18. Lead 16 carries one or more stimulation electrodes, and is tunneled into patient 20 via a percutaneous port 22. Percutaneous port 22 may be formed, for example, in the abdomen or lower back of patient 20. A pulse generator within trial stimulator 14 is electrically coupled to electrodes carried by lead 16. The electrodes are deployed proximate the spinal cord 24 of patient 20 for delivery of spinal cord stimulation, e.g., for alleviation of chronic pain. Trial stimulator 12 typically will be external to patient 20. In some embodiments, however, trial stimulator 12 may be configured for temporary implantation within patient 20.

In accordance with the invention, trial stimulator 12 stores multiple applications to selectively emulate the operation of different chronically implanted stimulators. Each application may include or be associated with a different set of instructions that, when executed, permit trial stimulator 12 to emulate the operation of a particular chronically implanted stimulator. If different chronic stimulators are available for spinal cord stimulation, for example, trial stimulator 12 may store applications that correspond to the respective chronic stimulators. In this manner, by selection of a corresponding application, trial stimulator 12 emulates a selected chronic stimulator, i.e., operates in a manner substantially similar to the selected chronic stimulator. Operation of different chronic stimulators may differ in terms of parameter settings, ramp rates, timing, multi-channel stimulation capabilities, and the like. Trial stimulator 12 permits emulation of the different chronic stimulators, including operational variations among the stimulators.

Each application stored by trial stimulator 12 corresponds to a different chronically implanted stimulator. An "application" generally refers to a set of machine-readable instructions that direct operation of trial stimulator 12 to substantially emulate the operation of a corresponding chronically implanted stimulator. The selected application may be a section of memory that contains the instructions or a pointer or other reference that identifies a location of the pertinent set of instructions. The machine-readable instructions in an application may be accompanied by data, which may define operands for the instructions. For example, the data may include stimulation parameters such as current or voltage amplitude, stimulation pulse rate, stimulation pulse rate, duration, timing, electrode combinations, electrode polarities, and the like. In some embodiments, the instructions associated with an application may be substantially identical to the instructions carried within the corresponding chronically implanted stimulator.

To support multiple applications, trial stimulator 12 may include one or more memory modules that store instructions associated with multiple applications. Each memory module may store instructions to support a particular application. Alternatively, instructions to support a given application may be distributed across multiple memory modules, along with instructions for other applications. In this case, a memory module may store portions of sets of instructions associated with multiple applications.

Upon selection of a particular application, trial stimulator 12 emulates the operation of a chronically implanted stimulator that corresponds to the application. Each memory module may be a discrete memory device such as volatile or non-volatile memory chip. Alternatively, a memory module may be a bank of memory or a set of contiguous or non-contiguous memory addresses within memory. In general, a memory module may refer to an independently addressable memory space that stores sets of instructions and data corresponding to one or more applications.

As discussed above, the different stimulation applications may correspond to different stimulators that deliver a similar therapy. More particularly, in the example of spinal cord stimulation, the applications may correspond to different stimulators designed to deliver spinal cord stimulation for alleviation of chronic pain. Alternatively, the applications may correspond to chronically implanted stimulators that deliver different types of therapy. For example, the applications may correspond to stimulators that deliver spinal cord stimulation, deep brain stimulation, gastrointestinal stimulation, or pelvic floor stimulation. In some embodiments, the applications may correspond to different types of therapy, as well as different stimulators designed to deliver each type of therapy. In addition, the applications may be targeted to particular types of disorders.

Trial stimulator 12 may select one of the applications from memory in response to a command received from external programmer 14. In this manner, external programmer 14 programs the trial stimulator to select a set of instructions for operation of the trial stimulator. A physician or patient 20 may operate external programmer to select a desired application, as well as particular programs or parameter values applied by trial stimulator 12. In some embodiments, trial stimulator 12 may itself include a user interface that permits a patient 20 to select applications and specify programs or parameter values. The user interface in trial stimulator 12 may be provided as an alternative, or in addition, to a user interface in external programmer 14. Upon selection of a particular application, trial stimulator 12 or external programmer 14 may present a user interface that is customized to the selected application.

In some cases, trial stimulator 12 may be configured to apply a default application unless and until patient 20 or physician enters a command to change the default application. Trial stimulator 12 or external programmer 14 may present a menu or other user interface medium for selection of applications to be applied by the trial stimulator. In response to a command specifying selection of a particular application, trial stimulator 12 may select a corresponding application from memory 32. In particular, trial stimulator 12 may load the instructions associated with an application, either entirely or in successive segments, into random access memory for execution by the trial stimulator. Loading of an application may involve any of a variety of standard memory access techniques.

In an exemplary embodiment, trial stimulator 12 stores instructions for four individual applications. Each memory module may contain the instructions for one stimulation application. Alternatively, the instructions for the stimulation applications may be spread across multiple memory modules. Accordingly, the number of applications need not correlate with the number of memory modules. When changing from one stimulation application to another, stimulation delivered by trial stimulator 12 may change substantially or only slightly, depending on the similarities between the chronic stimulators being emulated. For example, stimulation parameters, types of connected leads, electrode combinations and electrode polarities may change when using the trial stimulator for a different application. In general, trial stimulator 12 permits patient 20 to experience such differences so that different chronic stimulators may be accurately emulated for purposes of efficacy evaluation.

Trial stimulator 12 may have a housing constructed from a variety of materials, such as titanium, stainless steel, or a polymeric material. Because trial stimulator 12 is not implanted within patient 20, the housing may be constructed of any type of durable material sufficient to secure and protect the inner components, and not necessarily in keeping with the biocompatibility requirements usually associated with implanted stimulators. For example, the housing of trial stimulator 12 may be constructed of other materials such as polyurethane, polycarbonate, aluminum, or another strong polymer or metal alloy. In any event, the housing may be constructed for external use. The location of trial stimulator 12 may be at the side of the lower abdomen or the side of the lower back. In alternative embodiments, the housing of trial stimulator 12 may be constructed for internal, implanted use within a patient on a temporary basis. Accordingly, the principles of the invention need not be limited only to external stimulators, but also may be used with implanted stimulators.

In one embodiment, the stimulator may be located near percutaneous port 22. Percutaneous port 22 may be a surgically opened site in the skin to provide passage for lead 16 to enter patient 20. For spinal cord, gastrointestinal, or pelvic floor stimulation, as examples, percutaneous port 22 may be located near the lower abdomen or lower back of patient 20, and may be kept open and protected through the use of a ring type seal structure. Alternatively, the skin around percutaneous port 22 may be allowed to close directly around electrical lead 16. In either case, percutaneous port 22 may essentially limit the period of time a patient may use a trial stimulator due to the risk of infection. Lead 16 is flexible, electrically insulated from body tissues, and terminated with electrodes at the distal ends of the lead. The proximal end of lead 16 is electrically coupled to pulse generator 18 to conduct the stimulation pulses to a target stimulation site. In some embodiments, more than one electrical lead may be used to deliver stimulation.

Trial stimulator 12 may include telemetry electronics to communicate with external programmer 14. External programmer 14 may be a small, battery-powered, portable device that accompanies patient 12 throughout a daily routine. In this case, external programmer 14 may be referred to as the patient programmer. This patient programmer may also be compatible with a chronic implantable stimulator that provides the same therapy as the chosen stimulation application. If the trial stimulator therapy is successful, the patient may continue to use the same patient programmer. The use of the same patient programmer during trial stimulation and chronic stimulation can reduce patient learning time and increase patient convenience.

External programmer 14 may have a simple user interface, such as a button or keypad, and a display or lights. External programmer 14 may be a hand-held device configured to permit activation of stimulation and adjustment of stimulation parameters. The programmer 14 also may be capable of turning stimulation on or off. In some embodiments, trial stimulator 12 may be controlled through a series of buttons, switches, or small display located on trial stimulator 12. In this case, programmers may not be needed to program the stimulator 12 in some instances, or they may be used in addition to the controls located on trial stimulator 12.

Alternatively, external programmer 14 may form part of a larger device including a more complete set of programming features including complete parameter modifications, firmware upgrades, data recovery, or battery recharging in the event stimulator 12 includes a rechargeable battery. This alternative programmer may be function as a physician programmer operated by a physician to program, interrogate, and maintain trial stimulator 12 and, alternatively, chronically implantable stimulators. Additionally, the physician programmer may be capable of initially choosing one of the stimulation applications for therapy. The physician programmer also may be able to limit compatible patient programmers by specifically indicating one patient programmer for altering stimulation parameters.

A physician programmer may enable the trial stimulator 12 to be used with more than one patient. After trial therapy, the physician programmer may upload data from the trial stimulator 12 for evaluation of the therapy. This data may include stimulation parameters, delivered stimulation, therapy modifications, and the like. This data may be stored within the physician programmer for recovery at a later time. In some cases, if a trial is successful, stimulation parameters used during the trial may be directly downloaded to a chronic stimulator for continuation of effective stimulation therapy. After all data is recovered from the trial stimulation, the physician programmer may erase all data associated with a patient. Once cleared, the trial stimulator 12 may be ready for use by another patient.

If trial therapy is successful, lead 16 may be kept in place and connected to the implantable chronic stimulator. A lead 16 used within patient 20 may not be used in another patient, and should be discarded if a trial does not indicate chronic implantation. If a percutaneous extension is attached to lead 16 for trial stimulation, the percutaneous extension may be removed so that the lead may be directly coupled to the chronically implanted stimulator, e.g., by tunneling the proximal end of the lead to the site at which the chronic stimulator is implanted.

In some embodiments, system 10 may include multiple trial stimulators 12 to stimulate a variety of regions on spinal cord 22. Stimulation delivered by the multiple stimulators may be coordinated in a synchronized manner, or performed without communication between stimulators. Also, the electrodes may be located in a variety of sites on the spinal cord dependent on the particular therapy or the condition of patient 12. In the case of multiple trial stimulators, the chronic therapy may be conducted through the use of multiple implantable stimulators or just one implantable stimulator.

Figure 2:
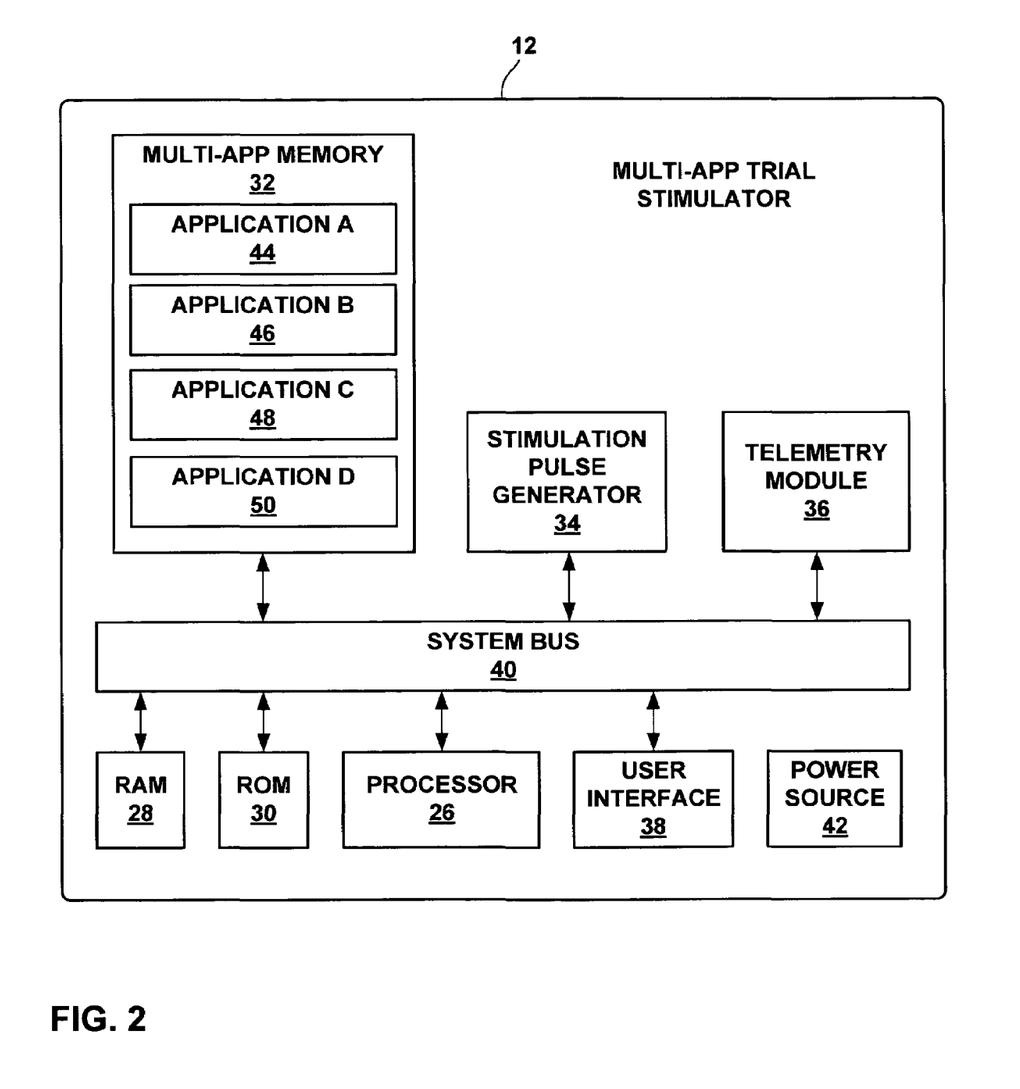
FIG. 2 is a functional block diagram illustrating various components of an exemplary multi-application trial stimulator.

FIG. 2 is a block diagram illustrating various components of an exemplary multi-application trial stimulator 12. As shown in FIG. 2, trial stimulator 12 may include a processor 26, random access memory (RAM) 28, read only memory (ROM) 30, multi-application memory 32, stimulation pulse generator 34, telemetry module 36, and an optional user interface 38, all of which may be coupled to a system bus 40 for control and exchange of data. Trial stimulator 12 further includes a power source 42, such as a rechargeable or non-rechargeable battery. Power source 42 may provide power to all components of trial stimulator 12.

Multi-application memory 32 may be a non-volatile electrically programmable read only memory, such as EEPROM, that stores instructions for multiple applications 44, 46, 48, 50 (also designated A, B, C, and D). Instructions for applications A, B, C, and D may be stored in respective memory modules, or distributed across multiple memory modules, such that portions of the instructions for each application may reside in each of the memory modules.

Processor 26 controls stimulation pulse generator 34 and telemetry module 36 via system bus 40. Stimulation pulse generator 34 generates stimulation pulses for delivery to patient 20 via lead 16. Processor 26 controls stimulation pulse generator 34 according to instructions associated with an application (A-D) 44, 46, 48, 50. The instructions for a given application (A-D) may specify stimulation parameters such as amplitude, pulse width, pulse rate, duration, timing, electrode combinations, electrode polarities, and the like.

RAM 28 provides a temporary memory space for execution of instructions associated with respective applications (A-D) 44, 46, 48, 50. For example, processor 26 may load operational instructions from ROM 30 for execution. ROM 30 may store firmware instructions associated with an operating system, which may be executed directly from ROM 30 to provide a shell operating environment or boot executive for processor 26. In addition, RAM 28 may store instructions associated with a selected application from multi-application memory 32.

Upon power up of trial stimulator 12, processor 26 executes the instructions from ROM 30. These instructions may also contain information relating to stimulation protocols, telemetry protocols, memory allocation guidelines and error handling. The contents of ROM 30 may also contain general information such as a stimulator identification number and manufacture history. Upon power up, processor 26 also may load a default application from one of applications 44, 46, 48, 50 into RAM 28. The default application may be identified by a flag in a register or memory associated with multi-application memory 32. Alternatively, processor 26 may present a menu to a patient 20 or physician for selection of a desired application, e.g., via user interface 38 and/or external programmer 14. In some embodiments, trial stimulator 12 may not include a user interface 38. Instead, user interface functionality, such as presentation of an application menu, may be provided entirely by external programmer 14.

Multi-application memory 32 may include multiple memory modules for the storage of instructions for the plurality of stimulation applications A, B, C, D. However, applications A, B, C, D may be stored within a contiguous mapping of memory space across the memory modules. As an illustration, each memory module could have a memory capacity of 32 Kbytes, such that four memory modules produce an overall memory space of 128 Kbytes within multi-application memory 32. For example, each memory module could be a 32 Kbyte EEPROM. In the example of FIG. 2, multi-application memory 32 contains four individual memory modules to store the instructions for a total of four stimulation applications A, B, C, D. However, the number of memory modules and associated stimulation applications may vary according to individual needs, and need not correlate with one another.

Multi-application memory 32 may be permanently contained within trial stimulator 12 or removable. Removable memory may be a type of EEPROM or FLASH memory, or multiple EEPROM or FLASH memories. For example, a CompactFlash or SmartMedia flash memory card may contain one or more individual memory modules. In some embodiments, a new flash memory card may be inserted into trial stimulator 14 with application updates or new stimulation applications. Alternatively, trial stimulator 12 may include a programming port that permits the contents of memory 32 to be rewritten. Examples of suitable programming ports for trial stimulator 12 are infrared (e.g., IrDa) ports, universal serial bus (USB), radio frequency (RF) ports, and the like.

Multi-application memory 32 may store different applications for a common type of therapy. For example, applications 44, 46, 48, 50 each may include instructions that correspond to different chronically implanted stimulators that address chronic pain by spinal cord stimulation. As an illustration, applications (A-D) 44, 46, 48, 50 could correspond to different neurostimulators manufactured by Medtronic, Inc., of Minneapolis, Minn., for spinal cord stimulation to alleviate chronic pain. For example, application A could correspond to the Medtronic Mattrix stimulator, application B could correspond to the Medtronic Itrel stimulator, application C could correspond to the Medtronic Synergy stimulator, and application D could correspond to the Medtronic RESTORE stimulator. In this manner, with trial stimulator 12, the physician may evaluate different types of chronic stimulators for a given type of stimulation or disorder. Likewise, the multiple applications may include instructions that correspond to different chronically implanted stimulators of a common type, but manufactured by different medical device manufacturers.

Alternatively, multi-application memory 32 may store different applications for different types of therapy. For example, applications 44, 46, 48, 50 each may include instructions that correspond to different chronically implanted stimulators for spinal cord stimulation, deep brain stimulation, gastrointestinal tract stimulation and pelvic floor stimulation. As an illustration, applications A-D could correspond to different stimulators manufactured by Medtronic, Inc., of Minneapolis, Minn., for such applications. For example, application A could correspond to the Medtronic RESTORE stimulator for spinal cord stimulation, application B could correspond to the Medtronic Activa stimulator for deep brain stimulation, application C could correspond to the Medtronic Enterra stimulator for gastrointestinal stimulation, and application D could correspond to the Medtronic Interstim stimulator for pelvic floor stimulation. In this manner, with trial stimulator 12, the physician may emulate different types of stimulators for a given patient 20 without the need to use different trial stimulators.

In addition to storing the instructions for the stimulation applications, memory 32 may contain additional data. This additional data may include patient information, selected parameters, patient actions and data generated during stimulation. For example, processor 26 may generate stimulation trend data and operational data that assists the physician in customizing the therapy for patient 20. The data may be recorded within memory modules of memory 32, or in separate memory. Memory 32 may contain all information to operate trial stimulator 12 for multiple stimulation applications and all data associated with the patient during the use of the pertinent stimulation applications. The data produced during use of a given application may be stored locally with the instructions for that application, or elsewhere within memory 32. In other embodiments, data produced by all applications may be stored together in a common area of memory 32.

Some data and instructions may be stored at multiple locations within trial stimulator 14. This redundancy may allow stimulation to continue unaffected if data corruption occurs. Once trial stimulator 12 is no longer used for one patient, all patient identifiable data may be erased before a different patient may use the trial stimulator. Further, patient identifiable data may be erased before the physician programmer may be allowed to program the trial stimulator 12 for a different patient. The erasure of patient data from trial stimulator 12 may be desirable for both privacy and safety reasons.

More or less memory modules may be contained within trial stimulator 12. For example, in some embodiments, trial stimulator 12 may only contain one large memory for storing all instructions and data associated with multiple applications. In this case, the applications may be segregated in different memory address regions, or otherwise mapped so that the applications can be readily retrieved and loaded for operation of trial stimulator 12. In other embodiments, many more memory modules may be included for separating data and limiting data corruption if one module fails. Moreover, as mentioned above, one memory module may contain instructions for more than one application, and one set of instructions for a given application may be split among more than one memory module.

In some embodiments, multiple applications A, B, C, D may be loaded into RAM 28 as software applications that run in an operating environment established by the contents of ROM 30. In this case, applications A, B, C, D operate as separate processes within the operating environment. The processes are identified as being active or inactive, or allocated processing cycles according to an active or inactive status. In this case, each application A, B, C, D runs on top of an operating system platform established by trial stimulator 12 from the instructions contained within ROM 30.

Alternatively, the instructions contained within ROM 30 may establish an operating system "shell" that permits trial stimulator 12 to "boot" into an operating environment created by one of applications A, B, C, D. In this case, applications A, B, C, D are not merely software applications running on an operating system. Instead, each application supports its own operating environment, which is launched from a shell operating system provided by instructions within ROM 30. In this manner, the contents of ROM 30 operate as a boot loader executive that causes trial stimulator to boot into one of applications A, B, C, D. This may be analogous to launching one of the Windows XP, Window NT, or Linux operating systems from a DOS shell in a standard computing system. In any event, trial stimulator 12 is able to selectively invoke one of the applications A, B, C, D by loading the corresponding contents of memory 32 into RAM 28.

When the code in ROM 30 executes upon power-up of trial stimulator 12, it looks for a flag set in memory 32 or elsewhere, which identifies the default application A, B, C, D into which the trial stimulator should boot. If no flag is set to identify a default application, trial stimulator 12 may communicate with external programmer 14, e.g., by wireless telemetry, to obtain a selected application. External programmer 14 may present a user interface menu to a user, such as a physician, for selection of a desired application A, B, C, or D. Upon receipt of a selection, the code in ROM 30 boots processor 26 of trial stimulator 12 into the selected application A, B, C, D, which then takes over operation of trial stimulator 12 for delivery of therapy. In this case, the application A, B, C, D booted by trial stimulator 12 may operate as the operating system for the trial stimulator.

External programmer 14 programs trial stimulator 12 to select one of the sets of instructions for operation of the trial stimulator. For example, trial stimulator 12 may set a corresponding flag in memory to identify the selected application communicated by programmer 14 as the default application, and then voluntarily reset the trial stimulator so that it reboots into the desired application on the resulting power-up initialization. Alternatively, trial stimulator 12 may set the corresponding flag in response to the command from external programmer 14 and then wait for a reset command from the external programmer 14. Hence, external programmer 14 may send both a default application selection command and a reset command. In either case, the selected application is loaded upon reset and is loaded into RAM 28 for operation. In this manner, trial stimulator 12 executes the application instructions and is able to emulate operation of a corresponding chronic stimulator.

Processor 26 controls the flow of data between RAM 28, ROM 30 and multi-application memory 32. Processor 26 copies the data required for operation and control of stimulation pulse generator 34 and places it within RAM 28 for fast and easy access. Alternatively, for instructions contained in ROM 30, processor 26 may execute the instructions directly from the ROM 30. Processor 26 uses the information stored within RAM 28 and multi-application memory 32 to control the stimulation generated by stimulation pulse generator 60. Based upon the stimulation instructions and parameters selected, processor 26 will determine when electrical pulses may be generated and delivered to patient 12. Processor 26 may also generate and store data during stimulation based upon the progress of therapy.

Wireless telemetry in stimulator 12 may be accomplished by radio frequency (RF) communication or proximal inductive interaction of trial stimulator 12 with external programmer 14 via telemetry module 36. Alternatively, because trial stimulator 12 will be ordinarily outside the body of the patient, wireless telemetry may be accomplished by other communication techniques such as infrared communication. As a further alternative, trial stimulator 12 and programmer 14 may communicate by wired communication. Processor 26 controls telemetry module 36 to exchange information with external programmer 14. Processor 26 may transmit operational information and sensed information to programmer 14 via telemetry module 36. Also, in some embodiments, trial stimulator 12 may communicate with other devices, such as stimulators or sensors, via telemetry module 36.

To support wireless telemetry, telemetry module 36 includes appropriate radio frequency transmit, receive, amplifier, filtering, antenna and modem components. In some embodiments, telemetry module 36 may alternatively or additionally provide wired communications. Because trial stimulator 12 is external to patient 20, a cable connection may be available when wireless telemetry is not desired. This connection may utilize a universal serial bus (USB) or similar circuitry to transfer information to another device.

Power source 42 delivers operating power to the components of trial stimulator 12. Power source 42 may include a battery and a power generation circuitry to produce the operating power. In some embodiments, the battery may be rechargeable to allow extended operation Recharging may be accomplished through proximal inductive interaction between an external charger and an inductive charging coil within trial stimulator 12. In other embodiments, an external power supply may use a cable to connect to trial stimulator 12 to charge the stimulator battery or provide direct power for stimulation.

Figure 3:
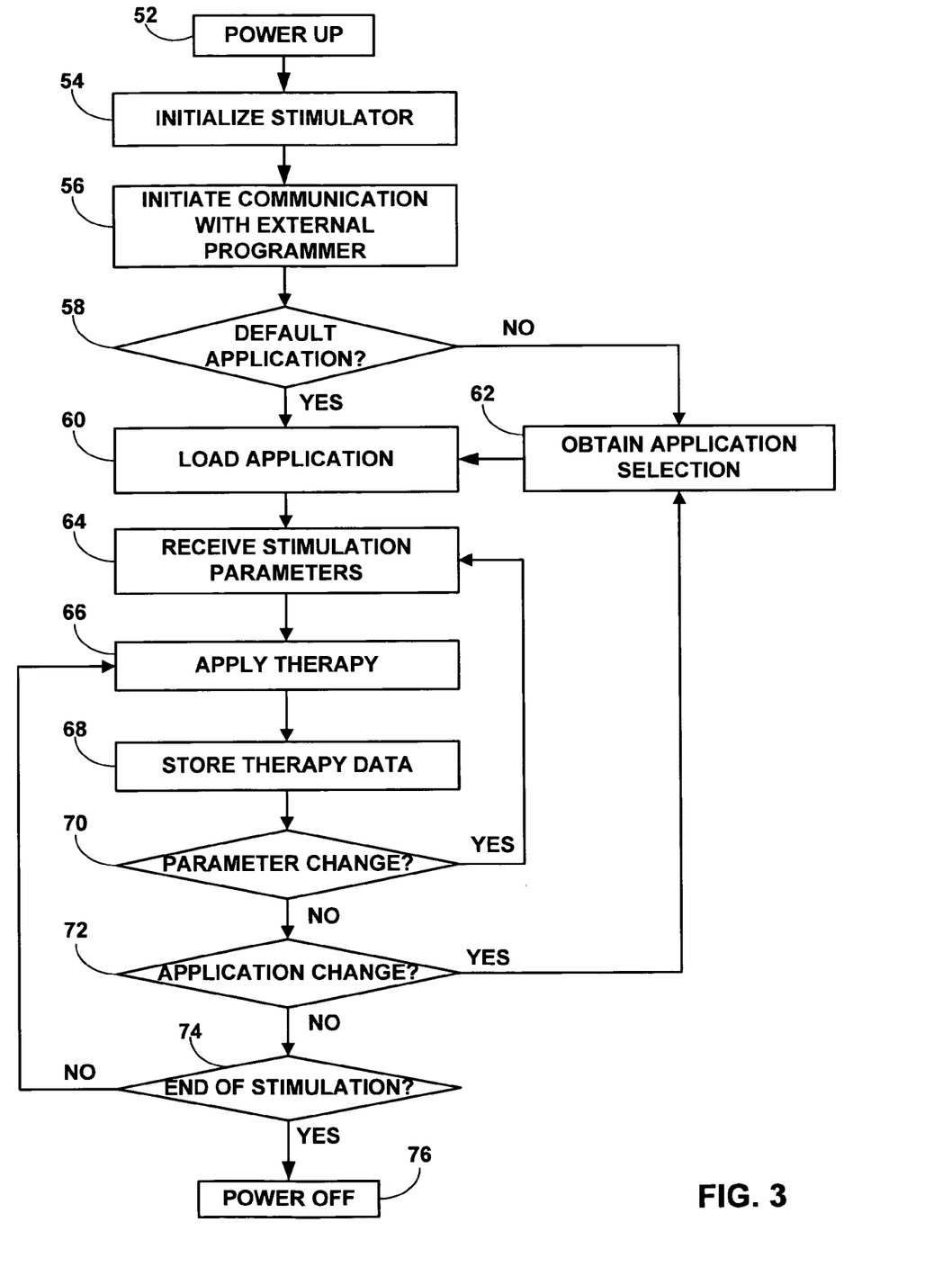
FIG. 3 is a flow diagram illustrating operation of a multi-application trial stimulator.

FIG. 3 is a flow diagram illustrating operation of a multi-application trial stimulator. As shown in FIG. 3, upon power up (52), processor 26 initializes trial stimulator 12 (54) and initiates communication with an external programmer (56). If a default application is specified (58), processor 26 loads the contents of a corresponding application from multi-application memory 32 (60). Again, the application may be one of multiple applications stored in multi-application memory 32. If no default application is specified, processor 26 obtains a user selection of an application (62), e.g., by presentation of a selection menu via a user interface associated with trial stimulator 12 or programmer 14.

As an example, if no default application is indicated, trial stimulator 12 may receive a selection from programmer 14, in which case trial stimulator 12 places a flag in memory to specify the selection as the default application. Following the selection, trial stimulator 12 may receive a reset command from programmer 14. In response, trial stimulator 12 executes a power-up reset operation and, upon initialization, loads the default application (60) that was specified just before the reset operation. Hence, selection of an application when no default is specified may involve selection by programmer 14, followed by a reset operation.

Once an application is loaded (60), processor 26 may continue to communicate with an external programmer, such as a patient programmer or physician programmer, to receive any stimulation parameters (64) or parameter changes that may be specified by a user for the application that is loaded in trial stimulator 12. Alternatively, in some embodiments, the parameters may be specified via a user interface provided in trial stimulator 12. Upon receipt of the stimulation parameters (64), trial stimulator 66 applies a therapy (66) that corresponds to the set of instructions associated with the loaded application and, in turn, corresponds to a particular chronically implanted stimulator. In this manner, trial stimulator 66 emulates operation of the chronically implanted stimulator.

In the course of therapy, processor 26 may store therapy data such as parameter changes, operational data, and the like (68). In some embodiments, the therapy data may be stored within a memory module, or other memory space, associated with the presently loaded application. If there is a parameter change (70) by a user, processor 26 receives stimulation parameters (64) and repeats application of therapy (66). Also, processor 26 may handle an application change (72) in which the user wants to switch to a different application. In this case, processor 26 obtains an application selection from the user (60) and loads the newly selected application into memory for delivery of a corresponding therapy, and emulation of a corresponding chronically implanted stimulator. The change to a newly selected application may be invoked by designation of the application as the default application, followed by a reset operation, as in the case in which no default application is specified. Typically, parameter changes may be performed using a patient programmer or physician programmer. However, application changes are preferably performed only by a physician using the physician programmer. When the end of stimulation is reached (74), either by expiration of a timer or active input from a user, the trial stimulator may be powered off (76).

In some embodiments, selection of an application and stimulation parameters may involve entry of a variety of information about the leads and stimulator that are to be emulated. For example, the physician may then use external programmer 14 to select the number and type of leads that will be used. Programmer 14 may then be used to set each stimulation parameter used for the selected stimulation application. The stimulation parameters may include different settings for amplitude, pulse width, pulse rate, electrode combination, electrode polarity, and the like. The degree to which a patient may later change parameters (70) may be subject to limits in order to ensure patient safety and comfort. Some parameter values may be automatically selected by trial stimulator 12, e.g., based on auto-sensing of lead and electrode configurations.

Various embodiments of the described invention may include processors, such as processor 26, that are realized by microprocessors, digital signal processors (DSPs), microcontrollers, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or non-volatile memory, including random access memory (RAM) such as static RAM (SRAM) or synchronous dynamic RAM (SDRAM), read-only memory (ROM), electronically programmable memory (EPROM or EEPROM), or Flash memory.

The techniques described herein may be implemented in a stimulation device in hardware, software, firmware, or any combination thereof If implemented in software, the software may be executed in a programmable processor, as described above. In that case, the software that executes the techniques may be initially stored in a computer readable medium, as described above, and loaded and executed in the programmable processor. Thus, this disclosure also contemplates a computer readable medium comprising machine-readable instruction that upon execution carry out one or more of the techniques described herein.

The invention claimed is:

1. An electrical stimulation system comprising:
   a trial stimulator device that generates electrical stimulation, the trial stimulator device having a memory storing multiple sets of instructions, wherein each set of instructions corresponds to one of a plurality of different chronic stimulator devices; and
   a programmer that programs the trial stimulator device to select one of the sets of instructions for operation of the trial stimulator device,
   wherein the trial stimulator device applies the selected set of instructions to emulate operation of a corresponding chronic stimulator device.

2. The system of claim 1, wherein the trial stimulator device includes a housing for external use.

3. The system of claim 1, wherein the sets of instructions correspond to different stimulator devices configured for a substantially common therapy.

4. The system of claim 3, wherein the substantially common therapy application is selected from the group consisting of spinal cord stimulation, deep brain stimulation, gastrointestinal stimulation and pelvic floor stimulation.

5. The system of claim 1, wherein the sets of instructions correspond to different chronic stimulator devices configured for different therapies.

6. The system of claim 5, wherein the different therapies include at least two of spinal cord stimulation, deep brain stimulation, gastrointestinal stimulation and pelvic floor stimulation.

7. The system of claim 1, wherein the trial stimulator device applies the selected set of instructions as a software application running on an operating system.

8. The system of claim 1, wherein the trial stimulator device loads the selected set of instructions as an operating system for the trial stimulator device.

9. The system of claim 7, wherein the sets of instructions are stored in the memory as multiple software applications, and the trial stimulator device executes the selected set of instructions as one of the software applications to emulate the operation of the corresponding chronic stimulator device.

10. The system of claim 8, wherein the trial stimulator device loads the operating system via a boot loader executive that causes the trial stimulator to load the selected set of instructions as an operating system.

11. The system of claim 1, further comprising one or more implantable leads electrically coupled to the trial stimulator device, wherein each of the leads includes one or more electrodes.

12. The system of claim 11, further comprising a percutaneous extension that electrically couples the implantable leads to the trial stimulator device.

13. The system of claim 1, wherein the trial stimulator device is an external neurostimulator device.

14. The system of claim 1, wherein the programmer is a physician programmer used by a physician to program the trial stimulator device.

15. The system of claim 14, further comprising a patient programmer used by the patient, wherein the patient programmer is compatible with a chronic stimulator device that operates according to instructions similar to the selected set of instructions.

16. The system of claim 1, wherein the programmer is configured to select one of the sets of instructions based on a user selection.

17. The system of claim 1, wherein the programmer further comprises a display that presents a menu for user selection of one of the sets of instructions, and wherein the programmer is configured to select one of the sets of instructions based on the user selection.

18. An electrical stimulator device comprising:
a stimulation generator that generates electrical stimulation;
a memory storing multiple sets of instructions, wherein each set of instructions corresponds to one of a plurality of different chronic stimulator devices; and
a processor that selects one of the sets of instructions to control operation of the stimulation generator, wherein the processor applies the selected set of instructions to emulate operation of a corresponding chronic stimulator device.

19. The stimulator of 18, further comprising a housing for external use.

20. The stimulator of claim 18, wherein the sets of instructions correspond to different chronic stimulator devices configured for a substantially common therapy.

21. The stimulator of claim 20, wherein the common therapy application is selected from the group consisting of spinal cord stimulation, deep brain stimulation, gastrointestinal stimulation and pelvic floor stimulation.

22. The stimulator of claim 18, wherein the sets of instructions correspond to different chronic stimulator devices configured for different therapies.

23. The stimulator of claim 22, wherein the different therapies include at least two of spinal cord stimulation, deep brain stimulation, gastrointestinal stimulation and pelvic floor stimulation.

24. The stimulator of claim 18, wherein the processor applies the selected set of instructions as a software application running on an operating system.

25. The stimulator of claim 18, wherein the processor loads the selected set of instructions as an operating system for the trial stimulator device.

26. The stimulator of claim 24, wherein the sets of instructions are stored in the memory as multiple software applications, and the processor executes the selected set of instructions as one of the software applications to emulate the operation of the corresponding chronic stimulator device.

27. The stimulator of claim 25, wherein the processor loads the operating system via a boot loader executive that causes the processor to load the selected set of instructions as an operating system.

28. The stimulator of claim 18, further comprising one or more implantable leads coupled to the stimulation generator, wherein each of the leads includes one or more electrodes.

29. The stimulator of claim 28, wherein the implantable leads are coupled to the stimulation generator via a percutaneous extension.

30. The stimulator of claim 18, wherein the trial stimulator device is an external neurostimulator device.

31. The stimulator of claim 18, wherein the processor is configured to select one of the sets of instructions in response to a command received from an external programmer, wherein the command is based on a user selection.

32. A method comprising:
storing multiple sets of instructions in a memory in a trial electrical stimulator device, wherein each set of instructions corresponds to one of a plurality of different chronic stimulator devices;
selecting one of the sets of instructions to control operation of a stimulation generator within the trial electrical stimulator device; and
applying the selected set of instructions to emulate operation of a corresponding chronic stimulator device.

33. The method of claim 32, further comprising generating electrical stimulation based at least in part on the selected set of instructions.

34. The method of claim 32, wherein the sets of instructions correspond to different chronic stimulator devices configured for a substantially common therapy.

35. The method of claim 34, wherein the common therapy application is selected from the group consisting of spinal cord stimulation, deep brain stimulation, gastrointestinal stimulation and pelvic floor stimulation.

36. The method of claim 32, wherein the sets of instructions correspond to different chronic stimulator devices configured for different therapies.

37. The method of claim 36, wherein the different therapies include at least two of spinal cord stimulation, deep brain stimulation, gastrointestinal stimulation and pelvic floor stimulation.

38. The method of claim 32, further comprising applying the selected set of instructions as a software application running on an operating system.

39. The method of claim 32, further comprising loading the selected set of instructions as an operating system for the trial electrical stimulator device.

40. The method of claim 38, wherein storing the multiple sets of instructions comprises storing the multiple sets of instructions in the memory as multiple software applications, and applying the selected set of instructions comprises executing the selected set of instructions as one of the software applications to emulate the operation of the corresponding chronic stimulator device.

41. The method of claim 39, wherein loading the selected set of instructions as an operating system comprises loading the operating system via a boot loader executive.

42. The method of claim 32, wherein the trial electrical stimulator device is an external neurostimulator device.

43. The method of claim 32, wherein selecting one of the sets of instructions comprises selecting one of the sets of instructions based on a user selection.

44. The method of claim 32, further comprising displaying a menu for user selection of one of the sets of instructions, wherein selecting comprises selecting one of the sets of instructions based on the user selection.

45. A device comprising:
   means for storing multiple sets of instructions in a memory in a trial electrical stimulator device, wherein each set of instructions corresponds to one of a plurality of different chronic stimulator devices;
   means for selecting one of the sets of instructions to control operation of a stimulation generator within the trial electrical stimulator device; and
   means for applying the selected set of instructions to emulate operation of a corresponding chronic stimulator device.

46. The device of claim 45, wherein the trial electrical stimulator device is an external neurostimulator device comprising an electrical stimulation generator that generates electrical stimulation, one or more percutaneously implantable leads electrically coupled to the electrical stimulation generator, each of the leads including one or more electrodes for delivery of the electrical stimulation.

47. The device of claim 45, further comprising means for loading the selected set of instructions as an operating system for the trial electrical stimulator device.

\* \* \* \* \*